United States Patent [19]

Yokoyama et al.

[11] Patent Number: 5,273,976
[45] Date of Patent: Dec. 28, 1993

[54] OCULAR HYPOTENSIVE AGENTS

[75] Inventors: Tomihisa Yokoyama; Masaharu Fukami; Mitsuru Kataoka, all of Tokyo, Japan

[73] Assignee: Sankyo Company, Limited, Tokyo, Japan

[21] Appl. No.: 964,662

[22] Filed: Oct. 22, 1992

Related U.S. Application Data

[62] Division of Ser. No. 503,803, Apr. 3, 1990, Pat. No. 5,175,161.

[30] Foreign Application Priority Data

Apr. 6, 1989 [JP] Japan ..................... 1-87785

[51] Int. Cl.$^5$ .................... A61K 31/53; A61K 31/50
[52] U.S. Cl. .................... 514/242; 514/247; 514/913
[58] Field of Search ................ 514/242, 247, 913

[56] References Cited

U.S. PATENT DOCUMENTS

| | | | |
|---|---|---|---|
| 4,011,321 | 3/1977 | Coates et al. | 514/236.5 |
| 4,885,293 | 12/1989 | Andrews et al. | 514/223.2 |
| 4,898,862 | 2/1990 | Morisawa et al. | 514/236.2 |
| 4,914,093 | 4/1990 | Morisawa et al. | 514/211 |

OTHER PUBLICATIONS

The Merck Index, Eleventh Edition (1989), p. 1488.
Goth, Medical Pharmacology, pp. 181–183, 1984.

*Primary Examiner*—Zohreh A. Fay
*Attorney, Agent, or Firm*—Frishauf, Holtz, Goodman & Woodward

[57] ABSTRACT

Pharmaceutical compositions and methods for treatment of eye disorders employ ocular hypotensive compounds of the formula (I)

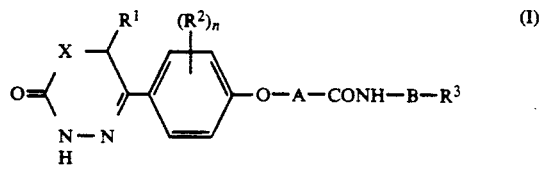

wherein $R^1$ is selected from hydrogen, $C_1$–$C_6$ alkyl, and $C_1$–$C_6$ alkoxy; each $R^2$ is selected from hydrogen, $C_1$–$C_6$ alkyl, halogen, nitro or carboxy; $R^3$ is selected from amino, mono-substituted amino, and di-substituted amino; A and B each represents $C_1$–$C_6$ alkylene, X represents —NH— or —CH$_2$— and n is 1, 2 or 3; and pharmaceutically acceptable salts or esters thereof.

14 Claims, No Drawings

OCULAR HYPOTENSIVE AGENTS

This is a division of application Ser. No. 07/503,803 filed Apr. 3, 1990, now U.S. Pat. No. 5,175,161, issued Dec. 29, 1992.

BACKGROUND OF THE INVENTION

This invention relates to pharmaceutical compositions with activity as ocular hypotensive agents, and methods for treatment of eye disorders by the application of ocular hypotensive compounds.

Typical compounds having ocular hypotensive activity include pilocarpine, physostigmine, and timolol, respectively of formula (A), (B), and (C);

OBJECTS OF THE INVENTION

An object of this invention is to identify ocular hypotensive compounds having activity in lowering intraocular pressure. A related object is compounds which can be formulated as eye drops or other ophthalmological formulations, and which are useful as therapeutic agents for treatment of glaucoma and/or ocular hypertension.

SUMMARY OF THE INVENTION

The present invention resides in the discovery of ocular hypotensive activity in compounds of the formula (I);

wherein:

$R^1$ represents a hydrogen atom, a $C_1$–$C_6$ alkyl group or a $C_1$–$C_6$ alkoxy group;

each $R^2$ is the same or different and represents a hydrogen atom, a $C_1$–$C_6$ alkyl group, a halogen atom, a nitro group or carboxy group;

$R^3$ represents a heterocyclic group, an amino group, or a mono- or di-substituted amino group, the substituents of the substituted amino group being selected from the group consisting of $C_1$–$C_6$ alkyl groups and $C_1$–$C_6$ alkyl groups having at least one substituent selected from the group consisting of substituents (a), substituents (a): phenyl groups, substituted phenyl groups with substituents selected from the group consisting of $C_1$–$C_6$ alkyl groups, $C_1$–$C_6$ alkoxy groups and halogen atoms, naphthyl groups, substituted naphthyl groups substituted with substituents selected from the group consisting of $C_1$–$C_6$ alkyl groups, $C_1$–$C_6$ alkoxy groups and halogen atoms, and heterocyclic groups;

A and B, which may be the same or different, each represents a $C_1$–$C_6$ alkylene group;

X represents a group of the formula —NH— or —CH$_2$—; and n represents 1, 2 or 3.

The heterocyclic groups have 5 to 7 ring atoms, including at least one nitrogen atom, and optionally have 1 to 3 further heteroatoms such as oxygen, sulphur and/or nitrogen. The heterocyclic groups are unsubstituted or have one substituent selected from a $C_1$–$C_6$ alkyl group, a $C_2$–$C_7$ aliphatic acyl group, a phenyl group and a substituted phenyl group substituted with a $C_1$–$C_6$ alkyl group, a $C_1$–$C_6$ alkoxy group or a halogen atom.

The compounds employed in this invention are phenyltriazinone or phenylpyridazinone derivatives. We are not aware of any reports of ocular hypotensive activity for any triazinone or pyridazinone.

With some exceptions, compounds of formula (I) are known from published EP 178189 and 238357. From these texts, the known compounds are reported to have therapeutic activity including cardiotonic activity, antihypertensive activity, activity in inhibition of gastric secretions and activity in inhibition of platelet aggregation, among other activities.

PREFERRED EMBODIMENTS OF THIS INVENTION

In the compounds of this invention, a $C_1$–$C_6$ alkyl group is a straight or branched alkyl groups having 1 to 6 carbon atoms such as a methyl, ethyl, propyl, isopropyl, butyl, isobutyl, sec-butyl, tert-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a straight or branched alkyl group having 1 to 4 carbon atoms and more preferably a methyl group.

In the compounds of this invention, a $C_1$–$C_6$ alkoxy group is a straight or branched alkoxy group having 1 to 6 carbon atoms such as a methoxy, ethoxy, propoxy, isopropoxy, butoxy, isobutoxy, sec-butoxy, tert-butoxy, pentoxy, isopentoxy, 2-ethylbutoxy, neopentoxy, 1-ethylpropoxy, hexyloxyl, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group, preferably a straight or branched alkoxy group having 1 to 4 carbon atoms and more preferably a methoxy group.

In the compounds of this invention, a halogen atom is typically fluorine, chlorine, bromine or iodine, and preferably fluorine or chlorine.

In the compounds of this invention, a $C_2$–$C_7$ aliphatic acyl group is illustrated by an acetyl, propionyl, butyryl, isobutyryl, valeryl, isovaleryl, pivaloyl, hexanoyl or heptanoyl group, preferably a $C_2$-$C_5$ aliphatic acyl group, and more preferably an acetyl group.

In the compounds of this invention, a mono- or di-substituted amino group is illustrated by a methylamino, dimethylamino, ethylamino, methylethylamino, diethylamino, propylamino, butylamino, pentylamino, hexylamino, benzylamino, o-, m- or p-methylbenzylamino, o-, m- or p-methoxybenzylamino, o-, m- or p-chlorobenzylamino, o-, m- or p-fluorobenzylamino, benzylmethylamino, phenylethylamino, phenylpropylamino, phenylbutylamino, naphthylmethylamino, naphthylethylamino, pyrrolidinoethylamino, piperidinoethylamino, morpholinomethylamino, morpholinoethylamino, morpholinoethylmethylamino, thiomorpholinoethylamino, piperazinoethylamino, 4-methylpiperazinoethylamino, 4-phenylpiperazinoethylamino, 4-acetylpiperazinoethylamino, 4-propionylpiperazinoethylamino, 2-pyridinylmethylamino, 2-pyridinylethylamino, 3-pyridinylethylamino, or 4-pyridinylethyl group, preferably a mono- or di-($C_1$-$C_4$ alkyl)amino group.

In the compounds of this invention, a heterocyclic group is a 5- to 7-membered (preferably 5 or 6 membered) heterocyclic group containing at least one nitrogen atom, optionally with 1 to 3 (preferably 1) further heteroatoms such as oxygen, sulphur, and/or nitrogen. Such heterocyclic groups are illustrated by a pyrrolidinyl, piperidinyl, hexahydroazepinyl, morpholinyl, thiomorpholinyl, piperazinyl, 4-methylpiperazinyl, 4-phenylpiperazinyl, 4-(o-, m- or p-methylphenyl)-piperazinyl, 4-(o-, m- or p-methoxyphenyl)piperazinyl, 4-(o-, m- or p-chlorophenyl)piperazinyl, 4-(o-, m- or p-fluorophenyl)piperazinyl, 4-acetylpiperazinyl, 4-propionylpiperazinyl, pyrrolyl, pyridinyl, 2-, 3-, or 4-methylpyridinyl, 2-, 3-, or 4-phenylpyridyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridazinyl, pyrimidinyl or pyrazinyl group, preferably a pyrrolyl, morpholinyl, thiomorpholinyl, pyrazolyl, pyridinyl, pyridazinyl, 4-methylpyridazinyl, 4-phenylpyridazinyl, 4-acetylpyridazinyl, pyrimidinyl, piperidinyl, piperazinyl or a pyrrolidinyl group, and more preferably a morpholinyl, thiomorpholinyl, piperazinyl, pyrrolidinyl, piperidinyl or pyridinyl group.

The $C_1$-$C_6$ alkylene group in the definitions of A and B is an alkylene group having 1 to 6 carbon atoms such as a methylene, methylmethylene, dimethylmethylene, propylmethylene, butylmethylene, 1-isobutylethylene, 1-methylethylene, 2-isobutylethylene, 2-methylethylene, 1,1-dimethylethylene, 2,2-dimethylethylene, 1-propylethylene, 2-propylethylene, 1-butylethylene, 2-butylethylene, ethylene, propylene, 1,1-dimethyltrimethylene, 2,2-dimethyltrimethylene, 3,3-dimethyltrimethylene, 1-propyltrimethylene, 2-propyltrimethylene, 3-propyltrimethylene, 1-butyltrimethylene, 2-butyltrimethylene, 3-butyltrimethylene, trimethylene, tetramethylene, 1-methyltrimethylene, 2-methyltrimethylene, 3-methyltrimethylene, pentamethylene or hexamethylene group. The group A is preferably a methylene, methylmethylene, ethylene, trimethylene or propylene group, and more preferably a methylene group. The group B is preferably an ethylene, propylene, trimethylene or tetramethylene group, and more preferably an ethylene group.

The compounds of general formula (I) can form salts, and these may be adopted for the present invention. In particular, compounds in which $R^2$ represents a carboxy group can form salts with bases, preferred salts of which include salts of an alkali metal or alkaline earth metal such as a sodium salt, potassium salt or calcium salt. Compounds (I) in which $R^2$ is not a carboxy group can form salts with acids, preferred salts of which include salts with an inorganic acid such as a nitrate salt, a perchlorate salt, a sulfate salt, a phosphate salt, or salts of a hydrohalogenic acid such as a hydrofluoride salt, hydrochloride salt, hydrobromide salt or hydroiodide salt; salts with a $C_1$-$C_6$ alkyl sulfonic acid salt such as a methanesulfonate salt, trifluoromethanesulfonate salt or an ethanesulfonate salt; salts with an arylsulfonic acid such as a benzenesulfonate salt or a p-toluenesulfonate salt; salts with an organic acid such as a fumarate salt, succinate salt, citrate salt, tartrate salt, oxalate salt, or maleate salt; or salts with an acidic amino acid such as a glutamate salt or aspartate salt.

The compounds of general formula (I) in which $R^2$ represents a carboxy group can form esters, and these may be adopted for the present invention. Examples of such esters include a $C_1$-$C_6$ alkyl ester; a $C_1$-$C_6$ alkyl ester having a substituent selected from phenyl, phenyl substituted with $C_1$-$C_6$ alkyl, $C_1$-$C_6$ alkoxy, or halogen, naphthyl or naphthyl substituted with $C_1$-$C_6$ alkyl, $C_1$-$C_6$ alkoxy or halogen; a phenyl ester; a phenyl ester having a substituent selected from $C_1$-$C_6$ alkyl, $C_1$-$C_6$ alkoxy or halogen; a naphthyl ester; or a naphthyl ester having a substituent selected from $C_1$-$C_6$ alkyl, $C_1$-$C_6$ alkoxy or halogen.

The compounds of general formula (I) may have an asymmetric carbon in the molecule, depending on the nature of certain substitutents. In such cases, stereoisomers will exist in the S-configuration and R-configuration. These individual isomers, or mixtures thereof, can be employed in the present invention.

Examples of preferred compounds of formula (I) include compounds of formula (II);

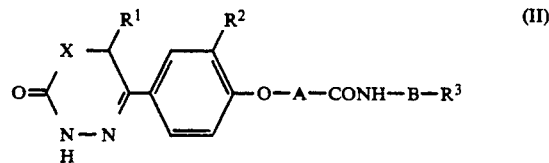

In such preferred compounds of formula (II), the following definitions are especially preferred, taken alone or in combination:

(1) $R^1$ is a hydrogen atom or a $C_1$-$C_4$ alkyl group, and more especially a hydrogen atom or a methyl group;

(2) $R^2$ is a hydrogen atom, methyl group, or a halogen atom, and more especially a hydrogen, fluorine or chlorine atom;

(3) $R^3$ is a 5–6 membered heterocyclic group, more especially a pyrrolyl, morpholinyl, thiomorpholinyl, pyrazolyl, pyridinyl, pyridazinyl, 4-methylpyridazinyl, 4-phenylpyridazinyl, 4-acetylpyridazinyl, pyrimidinyl, piperidinyl, piperazinyl or pyrrolidinyl group, and yet more especially a morpholinyl, thiomorpholinyl, piperazinyl, piperidinyl, pyrrolidinyl or pyridinyl group;

(4) $R^3$ is an amino group or a mono- or di-($C_1$-$C_4$ alkyl)amino group;

(5) A is a $C_1$-$C_2$ alkylene group, and more especially a methylene group;

(6) B is a $C_2$–$C_4$ alkylene group, and more especially an ethylene group;
(7) X is as defined; and/or
(8) n is 1.

Representative compounds of the present invention may include, for example, the numbered Compounds in the Table shown below, but the present invention is not limited to these compounds. Some of the Compounds are referred to again in this specification using these reference numbers.

In the following Table, various groups are identified by abbreviations, as follows:

| No. | $R^1$ | $R^2$ | $R^3$ | A | B | X |
|---|---|---|---|---|---|---|
| 1 | Me | Cl | mor | —$CH_2$— | —$CH_2CH_2$— | —NH— |
| 2 | H | Cl | mor | —$CH_2$— | —$CH_2CH_2$— | —$CH_2$— |
| 3 | Me | Cl | mor | —$CH_2$— | —$CH_2CH_2$— | —$CH_2$— |
| 4 | Me | Cl | 2-pyri | —$CH_2$— | —$CH_2CH_2$— | —$CH_2$— |
| 5 | H | Cl | 1-pyrr | —$CH_2$— | —$CH_2CH_2$— | —$CH_2$— |
| 6 | Me | H | mor | —$CH_2$— | —$CH_2CH_2$— | —NH— |
| 7 | Me | F | mor | —$CH_2$— | —$CH_2CH_2$— | —NH— |
| 8 | H | Cl | mor | —$CH_2$— | —$CH_2CH_2$— | —NH— |
| 9 | Me | Cl | thio-mor | —$CH_2$— | —$CH_2CH_2$— | —NH— |
| 10 | Me | Cl | 1-pipz | —$CH_2$— | —$CH_2CH_2$— | —NH— |
| 11 | Me | Cl | 4-me-1-pipz | —$CH_2$— | —$CH_2CH_2$— | —NH— |
| 12 | Me | Cl | 4-ph-1-pipz | —$CH_2$— | —$CH_2CH_2$— | —NH— |
| 13 | Me | Cl | 1-pipd | —$CH_2$— | —$CH_2CH_2$— | —NH— |
| 14 | Me | Cl | 1-pyrr | —$CH_2$— | —$CH_2CH_2$— | —NH— |
| 15 | Me | Cl | 2-pyri | —$CH_2$ | —$CH_2CH_2$— | —NH— |
| 16 | Me | Cl | 3-pyri | —$CH_2$ | —$CH_2CH_2$— | —NH— |
| 17 | Me | Cl | 4-pyri | —$CH_2$ | —$CH_2CH_2$— | —NH— |
| 18 | Me | Cl | mor | —$CH_2CH_2$— | —$CH_2CH_2$— | —NH— |
| 19 | H | H | mor | —$CH_2$— | —$CH_2CH_2$— | —NH— |
| 20 | H | H | mor | —$CH_2$— | —$CH_2CH_2$— | —$CH_2$— |
| 21 | Me | Cl | 4-ac-1-pipz | —$CH_2$— | —$CH_2CH_2$— | —$CH_2$— |
| 22 | Me | H | mor | —$CH_2$— | —$CH_2CH_2$— | —$CH_2$— |
| 23 | H | Cl | thio-mor | —$CH_2$— | —$CH_2CH_2$— | —$CH_2$— |
| 24 | Me | Cl | thio-mor | —$CH_2$— | —$CH_2CH_2$— | —$CH_2$— |
| 25 | Me | Cl | 1-pipz | —$CH_2$— | —$CH_2CH_2$— | —$CH_2$— |
| 26 | Me | Cl | 4-me-1-pipz | —$CH_2$— | —$CH_2CH_2$— | —$CH_2$— |
| 27 | Me | Cl | 4-ph-1-pipz | —$CH_2$— | —$CH_2CH_2$— | —$CH_2$— |
| 28 | Me | Cl | 1-pipd | —$CH_2$— | —$CH_2CH_2$— | —$CH_2$— |
| 29 | H | Cl | 1-pipd | —$CH_2$— | —$CH_2CH_2$— | —$CH_2$— |
| 30 | Me | Cl | 1-pyrr | —$CH_2$— | —$CH_2CH_2$— | —$CH_2$— |
| 31 | H | Cl | 2-pyri | —$CH_2$— | —$CH_2CH_2$— | —$CH_2$— |
| 32 | H | H | 2-pyri | —$CH_2$— | —$CH_2CH_2$— | —$CH_2$— |
| 33 | Me | Cl | 3-pyri | —$CH_2$— | —$CH_2CH_2$— | —$CH_2$— |
| 34 | Me | Cl | di-meam | —$CH_2$— | —$CH_2CH_2$— | —$CH_2$— |
| 35 | Me | Cl | bz-meam | —$CH_2$— | —$CH_2CH_2$— | —$CH_2$— |
| 36 | Me | Cl | moret-meam | —$CH_2$— | —$CH_2CH_2$— | —$CH_2$— |
| 37 | Me | F | mor | —$CH_2$— | —$CH_2CH_2$— | —$CH_2$— |
| 38 | Me | Cl | 4-pyri | —$CH_2$— | —$CH_2CH_2$— | —$CH_2$— |

Abbreviations
Me          methyl
mor         morpholino
2-pyri      2-pyridyl
3-pyri      3-pyridyl
4-pyri      4-pyridyl
1-pyrr      1-pyrrolidinyl
thiomor     thiomorpholino
1-pipz      1-piperazinyl
4-me-1-pipz 4-methyl-1-piperazinyl
4-ph-1-pipz 4-phenyl-1-piperazinyl
4-ac-1-pipz 4-acetyl-1-piperazinyl
1-pipd      1-piperidyl
dimeam      N,N-dimethylamino
bzmeam      N-benzyl-N-methylamino -continued

| No. | $R^1$ | $R^2$ | $R^3$ | A | B | X |
|---|---|---|---|---|---|---|
| moretmeam | | | N-morpholinoethyl-N-methylamino | | | |

Of the Compounds listed above, the preferred compounds are Compounds No. 1, 2, 3, 4, 5, 8, 15 and 31.

The compounds of formula (I) can be prepared by the synthetic procedures described in EP178189 or EP238357, or by appropriate modification of such procedures.

EXAMPLES OF THE INVENTION

The physiological activity and ocular hypotensive utility of compounds of this invention is illustrated by the following Test Examples 1 to 3.

The animals provided for the experiments of the Test Examples were male New Zealand white rabbits weighing around 2.5 kg, five in each group. After receipt, the rabbits were fed in a feeding chamber controlled at a temperature of 23° C., a relative humidity of 60% and lit for 12 hours (07:00 to 19:00), with free water intake and limited food intake. Rabbits with no detectable abnormalities in the eyes were employed for the experiments.

The samples for the Test Examples were prepared by dissolving the appropriate weight of the test compound in about 30–60 ml of 0.1N hydrochloric acid, and diluting the solution with 100 mM sodium phosphate buffer (pH 7.2) to adjust the pH to 5 to 7. For timolol maleate, 0.5% eye drop solution (Timoptol 0.5%, Santen Seiyaku) was used as such in the experiments.

TEST EXAMPLE 1

Activity on Elevation of Intraocular Pressure Induced by Water Load (the Water Load Test)

Rabbits were anesthetized with urethane (1.0 g/kg, i.v.), and the intraocular pressure of the eyes was measured. Immediately thereafter, 50 ml of the test sample using Compound 1 at a concentration of 0.2% was dropped on one eye, the experimental eye. On the other eye, as control eye, was dropped the same amount of diluent without test compound. Ninety minutes after application of the eye drops, the intraocular pressure was remeasured.

The water load test was then carried out. More specifically, tap water was orally administered compulsorily to the rabbit under anesthesia at a ratio of 60 ml per kg of body weight of rabbit, and thereafter the intraocular pressure of both eyes was measured with lapse of time.

| time | intraocular pressure (mmHg) | |
|---|---|---|
| (hr) | control eye | experimental eye |
| 1.5[a] | 17.1 ± 1.1 | 18.2 ± 1.1 |
| 2 | 32.4 ± 1.5 | 27.7 ± 1.4 |
| 2.5 | 27.1 ± 1.4 | 21.7 ± 1.5 |
| 3 | 22.8 ± 1.1 | 20.2 ± 1.8 |
| 3.5 | 21.5 ± 1.4 | 18.3 ± 1.5 |
| 4 | 20.1 ± 1.2 | 16.9 ± 1.5 |

[a]The water load was applied after the measurement at 1.5 hr.

A statistically significant difference (p<0.05, Paired t-test) was recognized for the intraocular pressure at 0.5 and 1.0 hour after water loading, i.e. at 2 and 2.5 hours, using the Compound 1 at 0.2%.

TEST EXAMPLE 2

Normal Intraocular Pressure Lowering Activity

The cornea surface of the rabbits was anesthetized with eye drops of oxybuprocaine (0.4% Benoxil, Santen Seiyaku). The rabbit intraocular pressure was measured by a pneumatic applanation tonometer (Alcon Applanation Pneumatonograph, Nippon Alcon). Measurement was conducted two or three times for each rabbit eye, and the average value was calculated and taken as the intraocular pressure, 25 ml of the test sample was dropped three times on one eye, the experimental eye, at intervals of 2 minutes. On the other eye, the control eye, was dropped the same amount of diluent without test compound. Then, the intraocular pressure of both eyes was measured with lapse of time.

In the following, the results when Compound 1 was used as the test sample at concentrations of 0.05%, 0.1% or 0.2% are given.

| time | intraocular pressure (mmHg) | |
|---|---|---|
| (hr) | control eye | experimental eye |
| Test Compound Concentration 0.05% | | |
| 0 | 19.6 ± 1.0 | 19.6 ± 1.0 |
| 0.5 | 22.5 ± 1.0 | 21.9 ± 1.1 |
| 1.0 | 20.7 ± 1.1 | 20.4 ± 0.7 |
| 2.0 | 21.8 ± 1.1 | 20.8 ± 1.6 |
| 3.0 | 22.8 ± 0.8 | 20.9 ± 1.0* |
| 4.0 | 23.4 ± 0.7 | 22.5 ± 1.3 |
| 5.0 | 22.3 ± 1.7 | 22.1 ± 0.9 |
| Test Compound Concentration 0.1% | | |
| 0 | 23.1 ± 0.9 | 23.1 ± 0.8 |
| 0.5 | 19.9 ± 1.0 | 19.9 ± 1.2 |
| 1.0 | 21.3 ± 0.9 | 21.5 ± 1.5 |
| 2.0 | 19.7 ± 0.6 | 19.1 ± 1.1 |
| 3.0 | 23.6 ± 0.8 | 20.4 ± 1.0* |
| 4.0 | 20.7 ± 0.4 | 18.5 ± 0.7 |
| 5.0 | 20.3 ± 0.9 | 18.4 ± 1.5 |
| 6.0 | 20.8 ± 1.0 | 19.5 ± 1.4 |
| 7.0 | 20.6 ± 0.6 | 19.3 ± 0.7* |

An asterisk (*) shows significant difference from the control eye ($p < 0.05$, Paired t-test).

| | Test Compound Concentration 0.2% | |
|---|---|---|
| time | intraocular pressure (mmHg) | |
| (hr) | control eye | experimental eye |
| 0 | 21.5 ± 0.8 | 21.5 ± 0.9 |
| 0.5 | 22.4 ± 1.6 | 21.7 ± 0.9 |
| 1.0 | 21.6 ± 1.3 | 19.4 ± 1.2* |
| 2.0 | 20.8 ± 0.9 | 18.9 ± 0.9* |
| 3.0 | 21.2 ± 0.7 | 18.1 ± 0.3* |
| 4.0 | 21.6 ± 1.0 | 17.5 ± 1.2* |
| 5.0 | 21.8 ± 1.0 | 19.4 ± 1.5* |
| 6.0 | 20.2 ± 1.0 | 18.4 ± 1.2* |
| 7.0 | 20.6 ± 1.4 | 19.2 ± 1.8* |

An asterisk (*) shows significant difference from the control eye ($p < 0.05$, Paired t-test).

The intraocular pressure for the control eyes and experimental eyes of the rabbits were similar, immediately before dropping of the test samples. For the 0.05% test sample, a significant lowering in intraocular pressure of 1.9 mm Hg was observed at 3 hours after eye dropping. For the 0.1% test sample, a significant lowering in intraocular pressure of 3.2 mm Hg and 1.3 mm Hg, respectively, was observed at 3 and 7 hours after eye dropping. Further, with the 0.2% test sample, a statistically significant ($p<0.05$, paired t-test) intraocular pressure lowering was exhibited in all the measurements from 1 hour to 7 hours after eye dropping. The maximum lowering in intraocular pressure was at 4 hours after eye dropping, and the difference in intraocular pressure between the control eye and the experimental eye reached 4.1 mm Hg.

Thus, an activity in lowering the intraocular pressure in the rabbit, dependent on the eye dropping concentration, was recognized.

TEST EXAMPLE 3

Normal Intraocular Pressure Lowering Activity

After anesthesia of the cornea surface of the rabbits with eye drops of oxybuprocaine (0.4% Benoxil, Santen Seiyaku), rabbit intraocular pressure was measured by a pneumatic applanation tonometer (Alcon applanation Pneumatonograph, Nippon Alcon). Measurement was conducted two or three times for each eye, and an average value was calculated to give the intraocular pressure value. After measurement of intraocular pressure, 25 ml of the test sample was dropped on one eye, the experimental eye, three times in total, at intervals of 2 minutes. On the other eye, the control eye, was dropped diluent without test compound. After completion of eye dropping, the intraocular pressure of the rabbits was measured with lapse of time.

Based on the measurement results, the intraocular pressure values of the control eyes and experimental eyes were plotted with the ordinate axis as intraocular pressure value, and the abscissa axis as time after eye dropping. The area of the region surrounded by the curve of the control eyes and that of the experimental eyes was calculated, and the values of the respective test substances were determined relative to a value of 1 for 0.5% timolol maleate. In this way, indices of the intraocular pressure lowering of the test compounds were established.

| Test Compound Number | Eye drop concentration (%) | Intraocular pressure lowering activity |
|---|---|---|
| 1 | 0.2 | 4.09 |
| 2 | 0.5 | 1.31 |
| 3 | 0.05 | 2.50 |
| 4 | 0.1 | 1.21 |
| 5 | 1.0 | 0.67 |

TEST EXAMPLE 4

Toxicity in Rat

Male F344 rats were used, five in each group. The Compound 2 was suspended in 0.5% CMC solution, and the suspension was orally administered at a ratio of 0.5 ml per 100 g of body weight of rat. Administration was performed every day at 9:00 for 4 days. After 24 hours of the final administration, the rat was anesthetized with ether, and blood and organs were enucleated, weighed and provided for pathologic examination.

The pathological examination did not reveal any significant effect resulting from the administration of the compound 2. The toxicity data was as follows:

| Dose (mg/kg) | 125 | 250 | 500 |
|---|---|---|---|
| Lethality | 0/5 | 0/5 | 1/5 |

These results indicate that the Compound 2 has no toxicity at a dose suited for therapy.

The ocular hypotensive agent of the present invention thus have good intraocular pressure lowering activity, and very low toxicity, and are useful as therapeutic agents for treatment of glaucoma and/or ocular hypertension.

The compound (I) of the present invention, is preferably administered in a dosage form which is an ophthalmological composition for topical administration to eyes, such as a solution, suspension, gel, ointment or solid insertion agent. These compositions can typically contain 0.001 to 10%, preferably 0.01 to 5% of the compound of the present invention. Although the compound of the present invention can be employed as the sole pharmaceutical, a β-blocker agent such as timolol maleate or pilocarpine, which is a parasympathetic nerve stimulant, can also be included.

The pharmaceutical preparation containing the active compound can be conveniently prepared by admixture with a nontoxic inorganic or organic carrier suited for opthalmological use. Typical pharmaceutically acceptable carriers are, for example, water; a mixture with water of a solvent miscible with water, such as a $C_1$-$C_6$ alkanol or aralkanol; vegetable oil, polyalkylene glycol; jelly with petroleum as the base; ethyl cellulose; ethyl oleate; carboxymethyl cellulose; polyvinyl pyrrolidone; isopropyl myristate; and other conveniently available acceptable carriers. The pharmaceutical preparation can also contain nontoxic auxiliary substances such as emulsifiers, preservatives, humectants, excipients, etc., including, for example, polyethylene glycol 200, 300, 400 or 600, carbowax 1,000, 1,500, 4,000, 6,000 or 10,000, a quaternary ammonium compound known to have low temperature sterilizability and nontoxic in use, an antibacterial agent such as a phenylmercury salt, thymerosal, methyl or propylparaben, benzyl alcohol, phenylethanol, one or more buffer agent components such as sodium chloride, sodium borate, and sodium acetate, gluconic acid buffer agents, and sorbitan monolaurate, triethanolamine, polyoxyethylene sorbitan monopalmitate, dioctylsodium sulfosuccinate, monothioglycerol, thiosorbitol, ethylenediaminetetraacetic acid, and other auxiliary substances.

Furthermore, suitable excipients for ophthalmology can be used as the carrier medium of the present invention, including conventional phosphate buffer excipient systems, isotonic borate excipients, isotonic sodium chloride excipients, isotonic sodium borate excipients, and other carrier media.

The pharmaceutical preparation can be made in the form of a solid insertion agent remaining in substantially complete state after administration of the drug, or as a biodisintegrable insertion agent which is soluble in tears or disintegrated by other methods.

Generally speaking, the compound of the present invention can be used in an amount of 0.001 to 50 mg, preferably 0.01 to 20 mg per kg of body weight. Depending on the necessary dose per day, administration can be made either singly or frequently, and also unit administration can be adopted.

In the following, the present invention is described in some more detail by reference to Preparation Examples for preparation of eye drop agents.

| Preparation example 1 | |
|---|---|
| Compound 1 | 0.2 g |
| Disodium phosphate | 0.716 g |
| Monosodium phosphate | 0.728 g |
| Sodium chloride | 0.4 g |
| Methyl p-hydroxybenzoate | 0.026 g |
| Propyl p-hydroxybenzoate | 0.014 g |

| -continued | |
|---|---|
| Preparation example 1 | |
| Sterlized pure water | q.s. |
| Hydrochloride acid | q.s. |
| Total amount | 100 ml |

The components were dissolved to prepare an eye drop solution in conventional manner.

| Preparation example 2 | |
|---|---|
| Compound 2 | 0.5 g |
| Disodium phosphate | 0.5 g |
| Monosodium phosphate | 1.1 g |
| Sodium chloride | 0.3 g |
| Benzethonium chloride | 0.01 g |
| Sterlized pure water | q.s. |
| Hydrochloride acid | q.s. |
| Total amount | 100 ml |

The components were dissolved to prepare an eye drop solution in conventional manner.

| Preparation example 3 | |
|---|---|
| Compound 5 | 1.0 g |
| Disodium phosphate | 0.4 g |
| Monosodium phosphate | 1.0 g |
| Sodium chloride | 0.69 g |
| 10% Benzalkonium chloride solution | 100 ml |
| Sterlized pure water | q.s. |
| Hydrochloric acid | q.s. |
| Total amount | 100 ml |

The components were dissolved to prepare an eye drop solution in conventional manner.

We claim:

1. A method for treatment of eye disorders by the application of an effective amount of an ocular hypotensive compound of the formula (I)

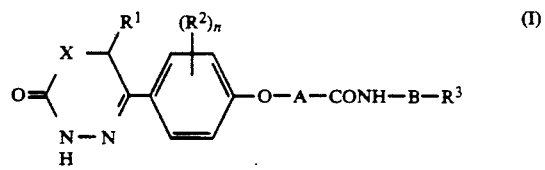

wherein:
$R^1$ is selected from the group consisting of a hydrogen atom, a $C_1$-$C_6$ alkyl group, and a $C_1$-$C_6$ alkoxy group;

each $R^2$ is the same or different and is selected from the group consisting of a hydrogen atom, a $C_1$-$C_6$ alkyl group, a halogen atom, a nitro group or a carboxy group;

$R^3$ is selected from the group consisting of an amino group, a mono-substituted amino group, and a di-substituted amino group, the substituents of the substituted amino groups being selected from the group consisting of unsubstituted $C_1$-$C_6$ alkyl groups and $C_1$-$C_6$ alkyl groups having at least one substituent selected from the group consisting of substituents (a), substituents (a): unsubstituted phenyl groups, phenyl groups substituted with substituents selected from the group consisting of $C_1$-$C_6$ alkyl groups, $C_1$-$C_6$ alkoxy groups and halogen atoms, unsubstituted naphthyl groups, naphthyl groups substituted with substituents selected from the group consisting of $C_1$-$C_6$ alkyl groups, $C_1$-$C_6$ alkoxy groups and halogen atoms;

A and B, which may be the same or different, each represents a $C_1$-$C_6$ alkylene group;

X represents a group of the formula —NH— or —CH$_2$—; and n represents 1, 2 or 3;

or a pharmaceutically acceptable salt or ester thereof.

2. The method of claim 1, in which said effective amount is in the range of 0.001 to 50 mg per kg of body weight.

3. The method of claim 1, in which said effective amount is administered in the form of an ophthalmological composition suited for topical administration to eyes and selected from a solution, suspension, gel, ointment and solid insertion agent.

4. The method of claim 1 wherein said ocular hypotensive compound is a compound of formula (II)

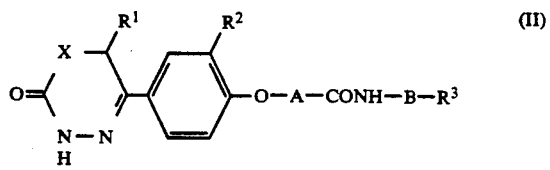

wherein $R^1$, $R^2$, $R^3$, A, B, and X are as defined in claim 1, or a pharmaceutically salt or ester of said ocular hypotensive compound.

5. The method of claim 1, wherein $R^1$ is a hydrogen atom or a $C_1$-$C_4$ alkyl group.

6. The method of claim 5, wherein $R^1$ is a hydrogen atom or a methyl group.

7. The method of claim 1, wherein $R^2$ is a hydrogen atom, a halogen atom or a methyl group.

8. The method of claim 1, wherein $R^2$ is a hydrogen or a halogen selected from the group consisting of a fluorine atom and a chlorine atom.

9. The method of claim 1, wherein $R^3$ is an amino group or mono- or di-($C_1$-$C_4$ alkyl) amino group.

10. The method of claim 1, wherein A is a $C_1$-$C_2$ alkylene group.

11. The method of claim 10, wherein A is a methylene group.

12. The method of claim 1, wherein B is a $C_2$-$C_4$ alkylene group.

13. The method of claim 1, wherein B is an ethylene group.

14. The method of claim 1, wherein n is 1.

* * * * *

UNITED STATES PATENT AND TRADEMARK OFFICE
CERTIFICATE OF CORRECTION

PATENT NO. : 5,273,976

DATED : December 28, 1993

INVENTOR(S) : YOKOYAMA et al

It is certified that error appears in the above-identified patent and that said Letters Patent is hereby corrected as shown below:

```
Column 11, line 1 (Claim 1):  after "groups" (first
         occurrence), delete "," and insert --and--.
```

Signed and Sealed this

Twenty-third Day of August, 1994

Attest:

BRUCE LEHMAN

Attesting Officer

Commissioner of Patents and Trademarks